US00PP08573P

United States Patent [19]

Wain

[11] Patent Number: Plant 8,573

[45] Date of Patent: Feb. 1, 1994

[54] CHRYSANTHEMUM PLANT NAMED 'WAIN'S PINK LADY'

[75] Inventor: Peter Wain, Hayling Island Hants, United Kingdom

[73] Assignee: Cleangro, Ltd., Havant, England

[21] Appl. No.: 899,672

[22] Filed: Jun. 12, 1992

[51] Int. Cl.[5] ..... A01H 5/00

[52] U.S. Cl. ..... Plt./80

[58] Field of Search ..... Plt. 76, 80

[56] References Cited

PUBLICATIONS

Sunnyslope Gardens Catalog. Chrysanthemums 1992. Pp. 3, 5.

Sunnyslope Gardens Catalog. Chrysanthemums 1987. Pp. 6, 8.

*Primary Examiner*—Howard J. Locker

*Attorney, Agent, or Firm*—Arnold, White & Durkee

[57] ABSTRACT

Chrysanthemum Wain's Pink Lady is a new cultivar, distinguished by its overall pink color with a rose colored eye, an exceptionally upright to spreading branching habit and good flowering characteristics. Wain's Pink Lady originated from a cross made by Peter Wain in a controlled breeding program in Havant, Hampshire, England. The female parent of Wain's Pink Lady was the commercial plant Pink Arola and the male parent was a numbered unnamed seedling designated "1 WX-87". Wain's Pink Lady was selected as one flowering plant from the progeny of the stated cross because of the unusual overall pink color of the flowers. The unique flower color is distinct from the lavender color of the female parent Pink Arola. Additionally, Wain's Pink Lady's contrasting rose colored eye makes its appearance even more distinguishable from either the male parent, 1 WX-87, or a commercially marketed Chrysanthemum named Charm which is similar in capitulum and habit to Wain's Pink Lady.

1 Drawing Sheet

BACKGROUND OF THE NEW PLANT

The new Chrysanthemum cultivar was among the progeny of a cross made by Peter Wain between the female parent Pink Arola (U.S. Plant Pat. No. 6,129) and an unnamed male Chrysanthemum plant designated "1 WX-87." The cross which produced Wain's Pink Lady was made as part of a controlled breeding program conducted in Havant, Hampshire, England. Selection of Wain's Pink Lady was based on the overall flat appearance of the capitulum, its exceptional upright to spreading habit, ease in control of plant height and, in particular, on the rose-pink bud color that contrasts with the pale red-purple ray color which give the flower a contrasting rose colored eye and an overall pink appearance. Wain's Pink Lady resembles the commercial Chrysanthemum Charm (U.S. Plant Pat. No. 5,502) in capitulum form and branching pattern, but is distinctly more pink in color.

Wain's Pink Lady was asexually reproduced from vegetative cuttings grown in a green house in Havant, England. Horticultural examination of controlled flowerings of successive plantings showed that the characteristics herein disclosed for Wain's Pink Lady are firmly fixed and retained through successive generations of asexual reproduction.

DESCRIPTION OF THE PHOTOGRAPH

Typical inflorescence and leaf characteristics of Wain's Pink Lady are illustrated in the accompanying color photograph showing a topview of the plant grown as a pinched spray pot mum with 5 cuttings in a 6.5" pot.

DESCRIPTION OF THE PLANT

The following is a detailed description of the new Chrysanthemum plant's characteristics. The plant was vegetatively reproduced and grown in a greenhouse in Nipomo, Calif. for test purposes. Observations were made on plants grown as unrooted cuttings directly stuck into 6.5" pots under natural conditions of temperature and daylength prevailing in Nipoma, Calif. during March–May, 1992.

Color designations are compared to the 1986 edition of R.H.S. Colour Chart, first published in 1966 by The Royal Horticultural Society, London, England. The B-Nine growth regulator referred to in the culturing procedures is 2,2-dimethyl hydrazide sold under the name of Daminozide or Alar and manufactured by Uniroyal.

Wain's Pink Lady has not been observed under all possible environmental conditions. The phenotype may vary significantly with variations in the environment such as temperature, light intensity and daylength.

The following characteristics have been repeatedly observed and are determined to be basic characteristics of Wain's Pink Lady, which in combination distinguish this Chrysanthemum as a new and distinct cultivar.

1. Flat capitulum form,
2. Decorative capitulum type,
3. Pale red purple color of the fully expanded ray florets,
4. Rose pink bud color that contrasts with the pale red purple ray color giving the flower a contrasting rose colored eye and an overall pink appearance,
5. An average of 8.5 flowers per break,
6. Exceptional upright to spreading habit with an average of 3.6 breaks after a single pinch,
7. Flowering response approximately 63 days from the start of short days,
8. Relatively ease in controlling plant height such that the finished height is 10–17 inches depending on pot size and market requirements.

Of the commercial cultivars known to the inventor, the most similar to Wain's Pink Lady is the cultivar Charm (U.S. Plant Pat. No. 5,502). Charm and Wain's Pink Lady are similar in capitulum form and type and branching pattern. Charm is normally grown as a disbud pot and the diameter across the capitulum when grown this way is 9.7 cm. Wain's Pink Lady is normally grown as a CBR (central bud removal) pot and the diameter of the capitulum when grown this way is 7.7 cm. Wain's Pink Lady has an average of 8.5 flowers per break compared to 6.2 flowers per break for Charm. Wain's Pink Lady has a much better habit than Charm when grown as a CBR/Spray pot which saves the time and cost of disbudding. The medium sized flowers and the excellent habit make the plant full and robust in appearance. Wain's Pink Lady has a fewer number of breaks after a pinch than Charm. Wain's Pink Lady takes approximately 6 days longer to flower than Charm. Wain's Pink Lady is very different in color from Charm; the color of Wain's Pink Lady gives the feeling and looks of a truly pink Chrysanthemum. This unusual soft pink color, excellent habit and flowering characteristics have not previously been available in a pot Chrysanthemum.

THE PLANT

Origin: Progeny of cross between female parent Chrysanthemum Pink Arola (U.S. Plant No. 6,129) and unnamed male parent Chrysanthemum seedling "1 WX-87."

*Botanic.*—*Dendranthema grandiflora.*

*Common name.*—Chrysanthemum.

*Cultivar name.*—Wain's Pink Lady.

*Coding.*—1-AC-AQ-88 (England); CG90-0074 (United States).

Characteristics:

*Form.*—Shrub, flat.

*Height.*—Medium to short. Finished height is relatively easy to control to range from 25 to 42.5 cm depending on pot size and market requirements.

*Growth habit.*—When grown in 6.5" pot with 1–4 applications of B-9, the total plant height from the bottom of the pot may be maintained at 40–45 cm (plant height 24–29 cm). When grown in a 4.5" pot with 1–4 applications of B-9, total plant height may be maintained at 25–30 cm.

Branching.—Upright and spreading with an average of 3.6 breaks when grown with one pinch as a spray pot.

Foliage: The foliage is uniformly dark green.

*Upper surface.*—R.H.S. 147A.

*Lower surface.*—R.H.S. 147B.

*Shape.*—Leaves are typically 5-lobed with less uniform indentations than Charm leaves.

*Length.*—Mature leaf length is typically 9.5 cm.

*Width.*—Mature leaf width is typically 5.7 cm.

INFLORESCENCE

Capitulum:

*Form.*—Flat.

*Type.*—Decorative.

*Face.*—About 7.7 cm diameter.

Ray florets:

*Color.*—Corolla color is pink (general tonality as observed from a distance of three meters. Front: Fully expanded outer ray floret: R.M.S. 62D. Back: Fully expanded outer ray floret: R.H.S. 62B. Front unfolded ray florets in flower center: R.H.S. 62A. Bud stage unexpanded outer ray floret front: R.H.S. 63D. Bud stage unexpanded outer ray floret back: R.H.S. 63C.

*Number.*—About 152.

*Shape.*—Elliptic.

*Length.*—About 3.7 cm.

*Width.*—1.22 cm.

*Flw/bk.*—About 8.5.

REPRODUCTIVE ORGANS

Androecium: Present in both ray and disc florets-insignificant: no pollen.

Gynoecium: Present in both ray and disc florets-insignificant.

Flowering response: Response is approximately 63 days from the start of short days.

What is claimed is:

1. A new and distinct Chrysanthemum cultivar, substantially as herein described and shown, characterized by an overall pink appearance accented by a rose colored eye contrasting with a pale red purple ray color.

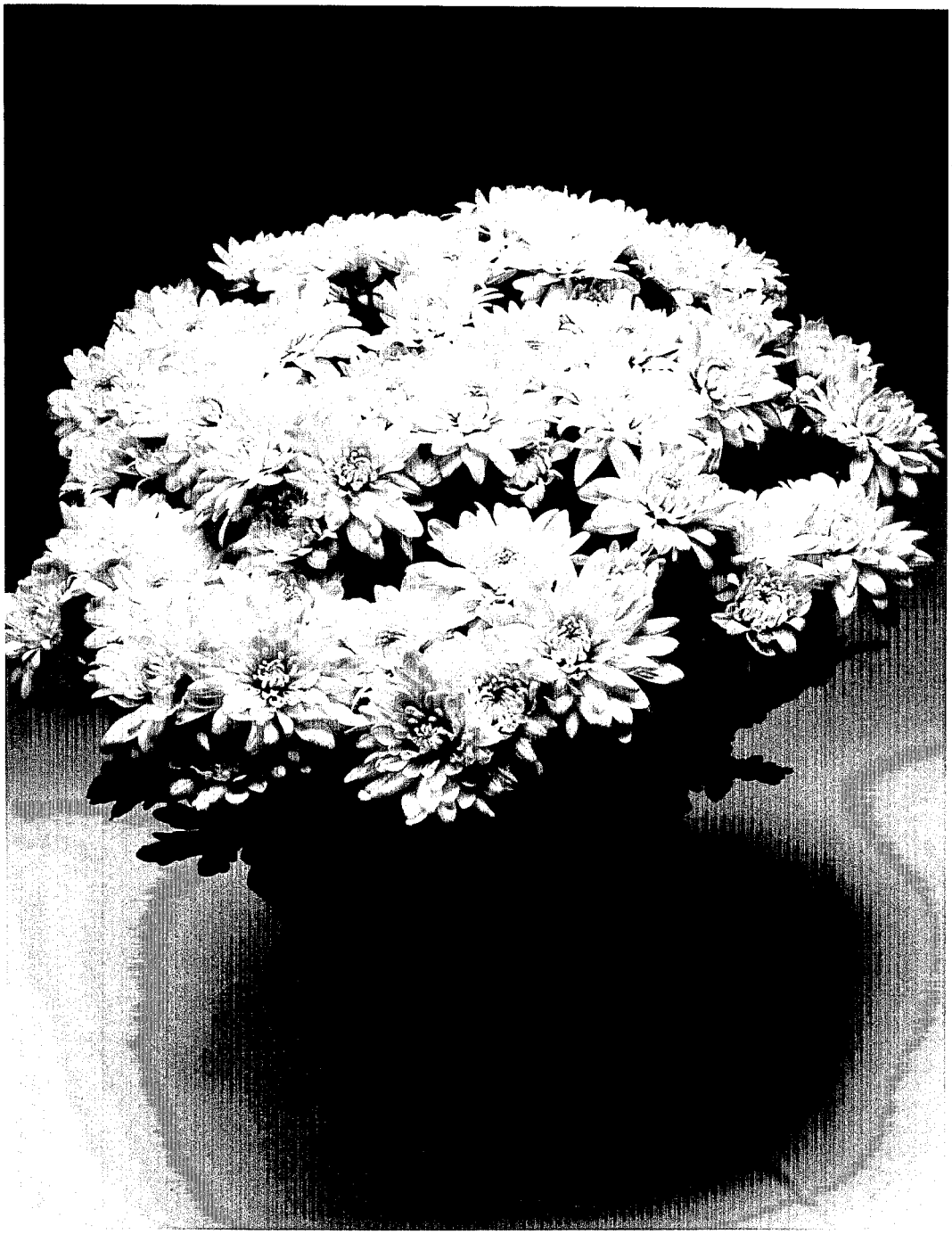

* * * * *